US00PP27608P3

(12) United States Plant Patent
Jones

(10) Patent No.: US PP27,608 P3
(45) Date of Patent: Jan. 24, 2017

(54) ***FUCHSIA* PLANT NAMED 'FWIDE16-1'**

(50) Latin Name: ***Fuchsia* hybrid**
Varietal Denomination: FWIDE16-1

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 123 days.

(21) Appl. No.: 14/121,826

(22) Filed: Oct. 20, 2014

(65) Prior Publication Data

US 2016/0113178 P1 Apr. 21, 2016

(51) Int. Cl.
*A01H 5/02* (2006.01)

(52) U.S. Cl.
USPC ..... Plt./300

(58) Field of Classification Search
USPC ..... Plt./300
See application file for complete search history.

*Primary Examiner* — Anne Grunberg
(74) *Attorney, Agent, or Firm* — Cassandra Bright

(57) ABSTRACT

A new and distinct *Fuchsia* cultivar named 'FWIDE16-1' is disclosed, characterized a vigorous but controlled growth and semi-pendulous plants suitable for commercial basket production. Flowers have a bright pink calyx and dark violet corolla; flowering response is not dependent upon day length. The new variety is a *Fuchsia*, typically produced as a garden or container plant.

2 Drawing Sheets

Latin name of the genus and species: *Fuchsia* hybrid.
Variety denomination: 'FWIDE16-1'.

BACKGROUND OF THE INVENTION

The new cultivar is a product of chance discovery. The new variety originated as a seedling discovered among a commercial planting of *Fuchsia* hybrid varieties. The parents are unknown. 'FWIDE16-1' was discovered by the inventor, Steve Jones, at a commercial greenhouse in Santa Paula, Calif. during Spring of 2012.

Asexual reproduction of the new cultivar 'FWIDE16-1' was first performed in Santa Paula, Calif. at a commercial greenhouse by vegetative cuttings in Summer of 2012. 'FWIDE16-1' has since produced several generations and has shown that the unique features of this cultivar are stable and reproduced true to type.

SUMMARY OF THE INVENTION

The cultivar 'FWIDE16-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FWIDE16-1'. These characteristics in combination distinguish 'FWIDE16-1' as a new and distinct *Fuchsia* cultivar:

1. Vigorous but controlled plant growth.
2. Highly floriferous plants.
3. Flowering response not dependent upon day length.
4. Distinctive bright pink calyx with dark violet corolla.
5. Attractive semi-pendulous plant habit.
6. Suitability for commercial basket production.

Plants of the new cultivar *Fuchsia* 'FWIDE16-1' are best compared to the commercial variety *Fuchsia* 'Kiefuter' U.S. Plant Pat. No. 13,773. The two *Fuchsia* varieties are similar in most horticultural characteristics; however, the new variety differs in the following:

1. The new variety has a deeper and brighter colored calyx near 52A, compared to the sepal color of 56A of 'Kiefuter'.
2. The new variety has deeper and brighter colored petals, colored brighter than Violet 86A, compared to the petal color of Purple 78A of 'Kiefuter'.
3. The new variety has more anthocyanin present in stems and veins, coloring stems and veins Greyed-Purple, whereas stems and veins of the comparator are green.
4. Comparison variety produces less flowers per plant.
5. Comparison variety produces larger flowers.

Plants of the new cultivar *Fuchsia* 'FWIDE16-1' can also be compared to the commercial variety *Fuchsia* 'FWIRP26-0' U.S. Plant Pat. No. 26,427. The two *Fuchsia* varieties are similar in most horticultural characteristics; however, the new variety differs in the following:

1. Plants of the new variety are more upright, growing almost twice as tall and just over half the width of the comparator.
2. The new variety has more anthocyanin present in veins, coloring veins Greyed-Purple, whereas veins of the comparator are green.
3. Comparison variety produces larger flowers.

BRIEF DESCRIPTION OF THE PHOTOGRAPHS

Figure 1:
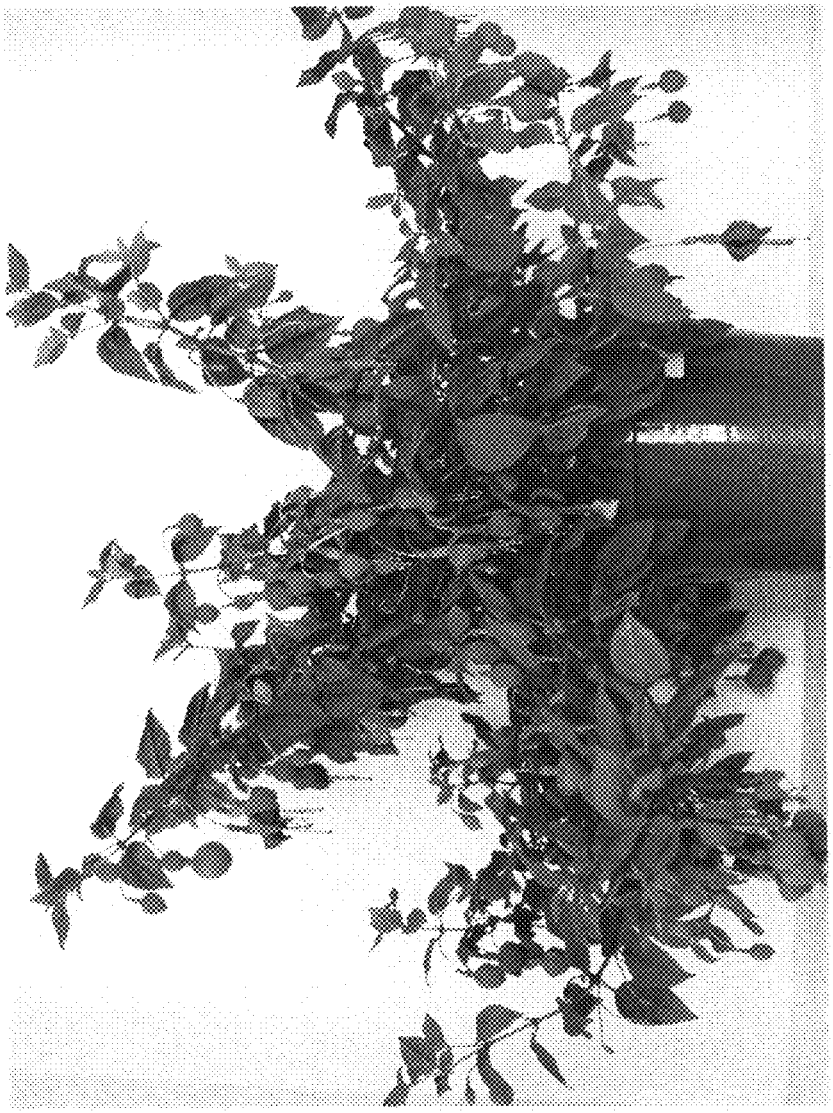
Figure 2:
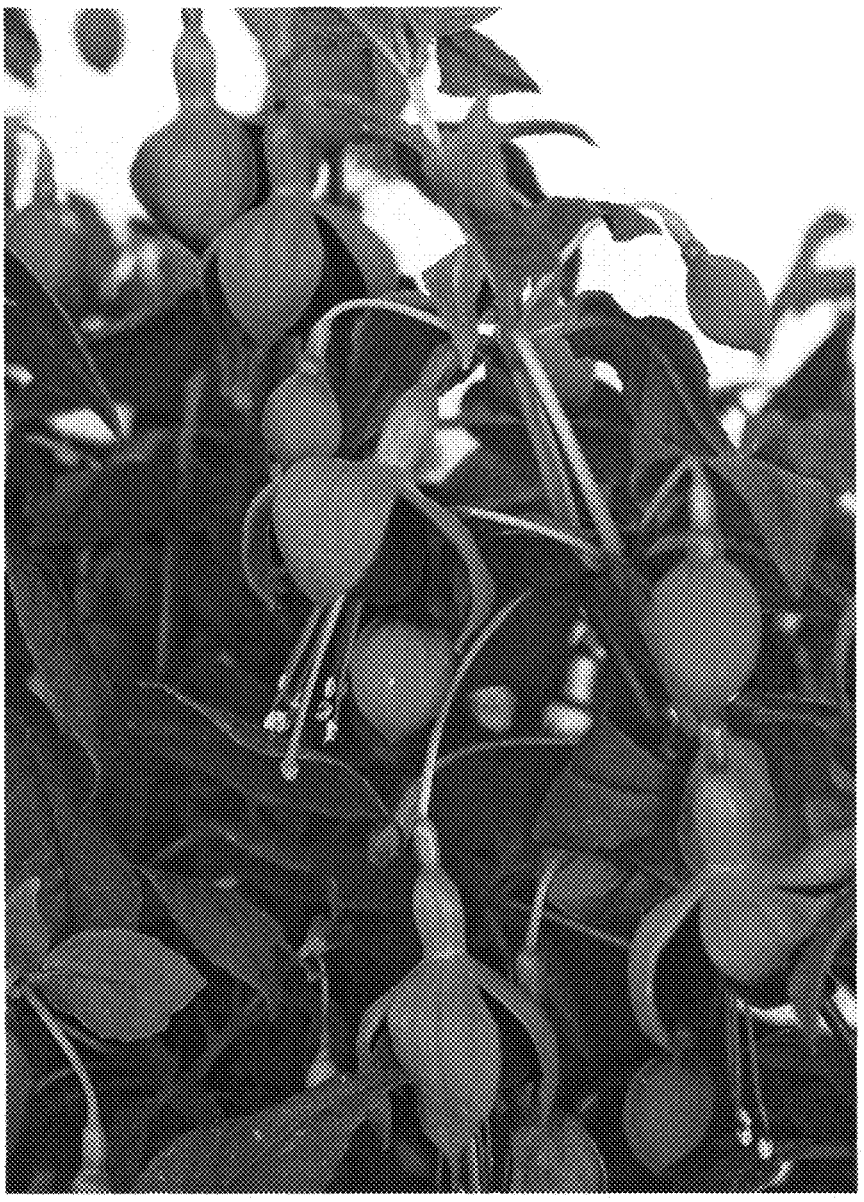

The accompanying photograph in FIG. 1 illustrates in full color a typical plant of 'FWIDE16-1' grown outdoors in Santa Paula, Calif. This plant is approximately 17 weeks old, shown in a 8 inch pot. FIG. 2 illustrates a close up of the flowers. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007, except where general terms of ordinary dictionary significance are used. The following observations and measurements describe 'FWIDE16-0'0 'FWIDE16-1' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Fuchsia* hybrid 'FWIDE16-1'.

PROPAGATION

Propagation method: Vegetative Cuttings.

Time to initiate roots: About 2 weeks at 15° C. to 22° C.

Root description: Fine, densely fibrous.

PLANT

Age of plant described: Approximately 17 weeks from 3 rooted cuttings.

Pot size of plant described: 8 inch.

Height: Approximately 41 cm from soil line of pot to top of foliar and uppermost flowering plane.

Plant spread: Approximately 58 cm.

Growth rate: Rapid.

Growth habit: Semi-erect and pendulous.

Branching characteristics: Free branching.

Length of primary lateral branches: Average 25 to 25 cm.

Diameter of lateral branches: Approximately 0.5 cm.

Quantity of primary lateral branches: Approximately 15.

Characteristics of primary lateral branches:

*Color*.—Near RHS Greyed-Purple 187A.

*Texture*.—Glabrous.

*Strength*.—Strong, flexible.

Internode length: Average range 1.2 cm to 2.5 cm.

FOLIAGE

Leaf:

*Arrangement*.—Opposite.

*Quantity*.—Approximately 18 to 22 fully expanded leaves per primary lateral branch.

*Average length*.—5.6 cm, including petiole.

*Average width*.—2.7 cm.

*Shape of blade*.—Ovate.

*Apex*.—Acute.

*Base*.—Oblique.

*Margin*.—Shallowly denate.

*Texture of top surface*.—Glabrous.

*Texture of bottom surface*.—Glabrous.

*Aspect*.—Mostly flat.

*Color*.—Young foliage upper side: Near RHS Green 137B. Young foliage under side: Near RHS Green 137C. Mature foliage upper side: Near RHS Green 139A. Mature foliage under side: Near RHS Green N138B.

*Venation*.—Type: Pinnate. Venation color upper side: Near RHS Greyed-Purple 187C. Venation color under side: Main vein near RHS Greyed-Orange 174C, flushed with Greyed-Purple 187B, lateral veins near Greyed-Purple 187B.

*Attachment*.—Stalked.

*Petiole*.—Length: Average 1.0 cm. Diameter: Average 0.2 cm. Texture: Glabrous. Color: Upper surface: Near RHS Greyed-Purple 183B. Lower surface: Near RHS Yellow-Green 146D, flushed Greyed-Purple 185A.

FLOWER

Natural flowering season: Spring.

Inflorescence and flower type and habit: 1 to 3 flowers emerge singly from each axil. Flowers emerge at different times, resulting in flowers of different maturity at each axil. Flowers are symmetrical and composed of a corolla surrounded by a decorative fused calyx. Flowers face outwardly.

Flowers per plant: Approximately 80 fully open flowers and 100 buds on a mature plant.

Flower longevity on plant: Approximately 1 week for individual flowers.

Persistent or self-cleaning: Self-cleaning.

Flower size (petals and sepals only, not including protruding stamen and style):

*Length*.—Approximately 2.5 cm.

*Width*.—Approximately 3.8 cm.

Bud:

*Shape*.—Oblong, with an inflated sphere at terminal end.

*Length*.—2.5 cm.

*Diameter*.—1.5 cm.

*Color*.—Near RHS Red 53C, with extreme brightness of appearance.

Corolla:

*Petals* (*measured from separation at top of tube*).—Number: Average 5 to 7. Length: Approximately 1.5 cm. Width: Approximately 1.7 cm. Shape: Orbicular. Aspect: Somewhat cupped or slightly undulating. Margin: Entire. Texture: Glabrous, all surfaces. Appearance: Matte. Apex: Obtuse. Color: When opening: Upper surface: Near RHS Violet 86A, but darker and deeper, very vibrant. Basal blotch near Red-Purple 58B. Lower surface: Near RHS Violet 86A, but darker and deeper, very vibrant. Basal blotch near Red-Purple 58B. Fully opened: Upper surface: Near RHS Violet 86A, but darker and deeper, very vibrant. Basal blotch near Red-Purple 58B. Lower surface: Near RHS Violet 86A, but darker and deeper, very vibrant. Basal blotch near Red-Purple 58B. Fading: Upper surface: Near RHS Violet 86B. Basal blotch near Red-Purple 58B. Lower surface: Near RHS Violet 86B. Basal blotch near Red-Purple 58B.

Calyx:

*Form*.—Funnel form base, separating approximately 25% from base, to flaring out into 4 large decorative deltoid shaped sepals. Sepals reflexed back.

*Fused section*.—Length: Approximately 1.0 cm. Diameter: Approximately 0.8 cm.

*Unfused section*.—Length: Approximately 2.7 cm. Diameter: Approximately 1.5 cm.

*Sepal texture*.—Glabrous all surfaces.

*Appearance*.—Bright and vibrant, not iridescent.

*Apex*.—Acute.

*Color*.—Upper Surface: Near RHS Red 52A, but brighter. Lower Surface: Near RHS Red 53C.

Fragrance: None.

Peduncle:

*Length*.—Average 2.5 cm.

*Diameter*.—0.1 cm.

*Color*.—Near RHS Yellow-Green N144D, slight flush of Greyed-Purple N186C.

*Texture*.—Glabrous.

REPRODUCTIVE ORGANS

Stamens:

*Number* (*per flower*).—Typically 8.

*Filament length*.—Average 2.9 cm.

*Filament color*.—Near RHS Red-Purple 58B.

*Anthers*.—Shape: Globular. Length: Approximately 0.1 cm. Color: Near RHS Greyed-Purple 187D.

*Pollen*.—Amount: Scarce, colored Orange-White 159C.

Pistils:

*Quantity per flower*.—1.

*Length*.—Approximately 5.3 cm.

*Style*.—Length: Approximately 4.7 cm. Color: Base near RHS Red-Purple 62D, upper ⅔ near Red-Purple 58B.

*Stigma*.—Shape: Globular. Color: Near Red-Purple 61C. Ovary: Length: Approximately 0.7 cm. Diameter: Approximately 0.4 cm. Color: Near RHS Green 139B.

OTHER CHARACTERISTICS

Seeds and fruits: Not observed to date.

Disease/pest resistance: Neither resistance nor susceptibility to normal diseases and pests of *Fuchsia* has been observed.

Temperature tolerance: Tolerates temperatures from approximately −1 C to 38 C.

Drought tolerance: No tolerance for drought.

What is claimed is:

1. A new and distinct cultivar of *Fuchsia* plant named 'FWIDE16-1' as herein illustrated and described.

* * * * *